United States Patent [19]

Claudy et al.

[11] Patent Number: 4,925,314
[45] Date of Patent: May 15, 1990

[54] DEVICE FOR DETECTING A THERMAL PHENOMENON OCCURRING IN A PRODUCT

[75] Inventors: Pierre Claudy, Brignais; Jean-Marie Letoffe, Decines Charpieu; Jean-Claude Commerçon, Caluire et Cuire, all of France

[73] Assignee: Institut Francais du Petrole, Rueil-Malmaison, France

[21] Appl. No.: 286,296

[22] Filed: Dec. 19, 1988

[30] Foreign Application Priority Data

Dec. 17, 1987 [FR] France .................. 87 17626

[51] Int. Cl.⁵ .................. G01K 1/14; G01N 25/12
[52] U.S. Cl. .................. 374/16; 374/10; 374/27
[58] Field of Search .................. 374/16, 17, 18, 20, 374/25, 10; 250/222.2

[56] References Cited

U.S. PATENT DOCUMENTS

| | | |
|---|---|---|
| 3,412,599 | 11/1968 | Hammons et al. .................. 374/17 |
| 3,527,082 | 9/1970 | Pruvot et al. .................. 374/17 |
| 4,075,475 | 2/1978 | Risby et al. .................. 250/282 |
| 4,240,284 | 12/1980 | Nguyen .................. 374/20 |
| 4,672,218 | 6/1987 | Chrisman et al. .................. 250/222.2 X |
| 4,770,540 | 9/1988 | Chague et al. .................. 374/17 |
| 4,804,274 | 2/1989 | Green .................. 374/17 |

FOREIGN PATENT DOCUMENTS

| | | | |
|---|---|---|---|
| 7550 | 1/1983 | Japan .................. | 374/17 |
| 1438754 | 6/1976 | United Kingdom .................. | 374/18 |

Primary Examiner—Daniel M. Yasich
Attorney, Agent, or Firm—Antonelli, Terry & Wands

[57] ABSTRACT

A device for detecting and/or measuring a thermal phenomena occurring in a product showing a liquid state at a temperature within the range of temperatures swept by the detecting and/or measuring device. An enclosure is provided with a calorimetric head containing at least one measurement cell which is adapted to be filled and emptied. Heat is transferred to the cell and a magnitude relating to a temperature of the cell is measured so as to obtain desired information regarding the product.

7 Claims, 2 Drawing Sheets

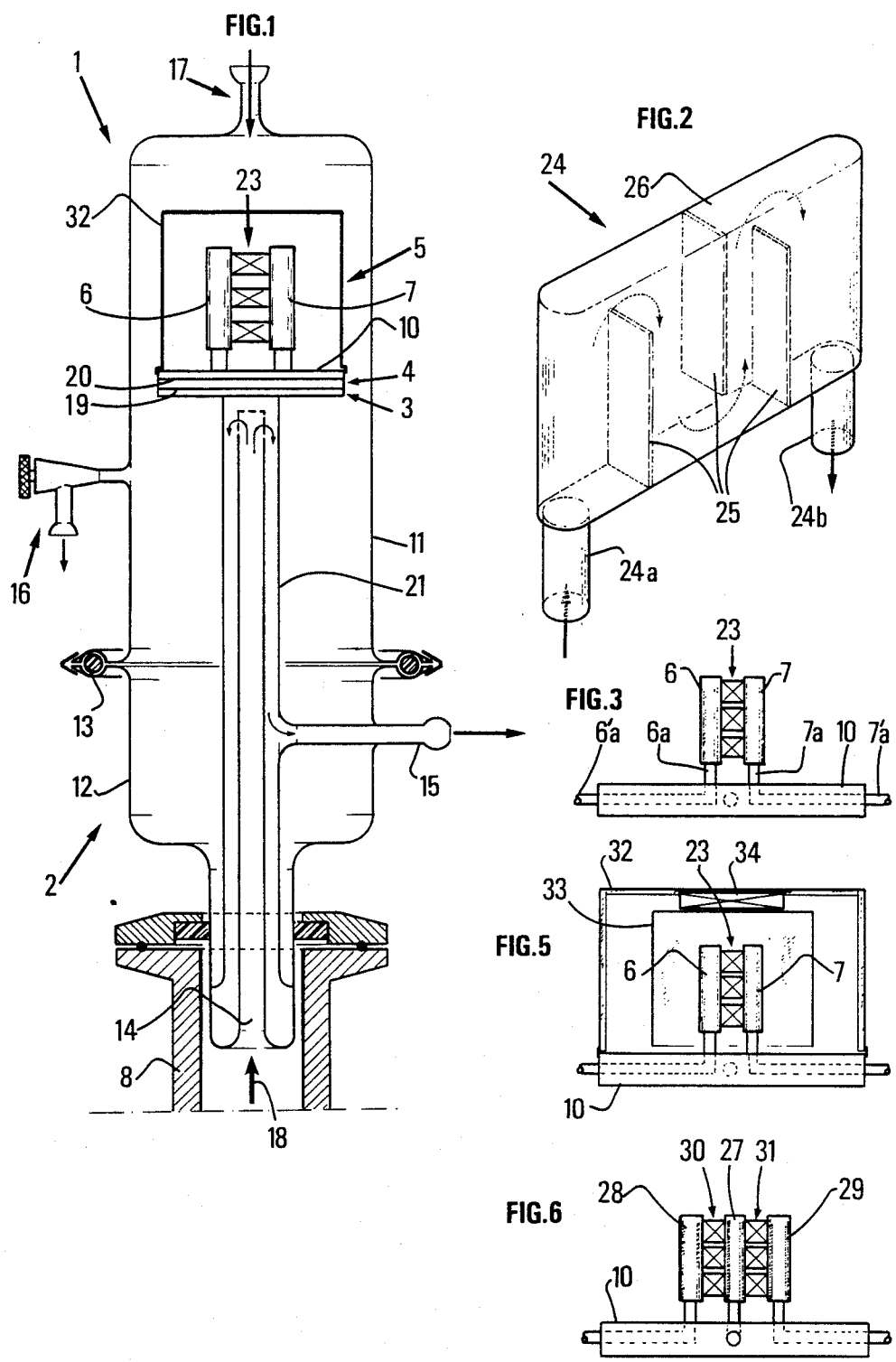

DEVICE FOR DETECTING A THERMAL PHENOMENON OCCURRING IN A PRODUCT

BACKGROUND OF THE INVENTION

1. Field of the Invention

The present invention relates to a device for detecting and/or measuring a thermal phenomenon occurring in a product in a liquid state at a temperature in the range of temperatures swept by the detecting and/or measuring device.

The detecting and/or measuring device of the invention makes it possible to obtain the desired information regarding a product rapidly and accurately and permits easy automation of the acquisition of the detected values from the beginning of the thermal effect such, for example, as the temperature at which a phase change appears and/or more complete measurements.

The device of the invention is particularly well adapted to the determination of the beginning crystallization temperature of paraffins in diesel fuels.

2. Description of the Prior Art

Fuels for diesel engines have an increasing economic importance. The fuels can be roughly likened, from the point of view of their composition, to a solution of n-paraffins in a complex hydrocarbonated matrix. Because of the nature of diesel fuels, special problems are raised when the temperature of use is lowered and, for example, paraffin crystals appear, which causes difficulties, even making operation of the diesel engine impossible.

The fuels must then comply with requirements which, in France, are laid down by the Direction des Carburants which define Three relevant temperatures as follows:

PT: cloud point, or temperature at which the first paraffin crystals appear,

TLF: limiting filtrability temperature, at which the paraffin crystals obstruct a mesh (45 $\mu$m) of the fuel filter, and PE: flow point, i.e. the temperature at which a three dimensional paraffin network is created and the fuel can no longer flow.

American standards (A.S.T.M.) or European (E.N.) define the devices which permit determination of these three temperatures. As far as the cloud point is concerned, it is a question of the standard A.S.T.M. D-9766. The apparatus used is very unsophisticated, since it is by direct visual observation of a cooled product that the point is detected at which the first paraffin crystals appear. The accepted reproducibility is 4° C.

An apparatus based on the principle of light diffusion have been constructed and is at the present time commercialized by, for example Normandie Labo, Malvern or Total.

Another method seems just as simple resides in detecting a release of heat by sweep calorimetry (A.C.D) when the first paraffin crystals are formed during cooling, i.e., when, in the n-constituent diagram, the liquidus is passed. It has been discovered that there was a linear relation between the measurement of the cloud point in accordance with the A.S.T.M. standard and the A.C.D. measurement. Similarly, the TLF and the PE may be found by A.C.D. with however non doped products. The reproducibility of the measurements is better than 0.1° C., which is much better than the ASTM standard.

In some cases, the standard leads to erroneous results. In fact, in order to obtain the best yield from a noble product crude, refiners more often used heavy fraction cracking which leads to clear oils (L.C.O.) then mixed with the distilled fractions.

In these fuels, at the time of cooling, an unmixing can be observed (passing from one to two liquids) interpreted visually as being the cloud point. This error does not affect the A.C.D., which always observes the beginning of crystallization of the paraffins.

SUMMARY OF THE INVENTION

The aim underlying present invention essentially resides in providing a detecting and/or measuring device, particularly for use in the above-described manner which allows a convenient use of the device by uninformed persons and, for this purpose, a measuring and/or detecting apparatus which is independent and requires no operation other than starting up and supplying with samples.

A further object of the present invention resides in providing a detecting and/or measuring device which enables an analysis of the results by a program designed as a function of the products to be studied thereby eliminating any error related to the observer or lack of experience of the observer.

More generally, the present invention relates to a device for detecting and/or measuring the thermal phenomenon occurring in a liquid comprising an enclosure with a calorimetric head containing at least one cell and means for measuring a magnitude related to the temperature of the cell or to the heat flux exchanges with this cell, as well as means for filling the cell with the liquid and heating the cell.

The device according to this invention further comprising means for adjusting the enclosure temperature. These means which can also be called sweep temperature means are adapted to change the temperature of the enclosure containing the measurement cell within a predetermined temperature range including a temperature for which the processed liquid is subjected to a thermal phenomenon.

The detecting and/or measuring device of the present invention may include an additional cell or may comprise at least two measurement cells.

Furthermore, the device of the invention may comprise at least two measurement cells and at least one thermopile placed between the measurement cell and a reference cell or any other means for measuring the exchange of flux with a reference such as fluxmeters.

The cells of the present invention may be placed on a base made from a material having good heat conducting characteristics, and the base may comprise at least one portion of a circuit for supplying the cell with liquid. Moreover, the base may be in contact with the heat transfer means.

BRIEF DESCRIPTION OF THE DRAWINGS

The present invention will be better understood and its advantages will be clearer from the following description of several embodiments, in no wise limitative, illustrated by the accompanying drawings in which:

FIG. 1 is a schematic view of a detecting and/or measuring device constructed in accordance with the present invention;

FIG. 2 is a perspective view of a measurement cell for a detecting and/or measuring device in accordance with the present invention;

FIG. 3 is a schematic view of a supply of the cells of the detecting and/or measuring device for the present invention;

FIG. 5, is a schematic view of calorimetric head comprising an intermediate compensating screen;

FIG. 6 is a schematic view of one embodiment of a detecting and/or measuring device in accordance with the present invention having three cells.

DESCRIPTION OF THE PREFERRED EMBODIMENTS

Figure 4:
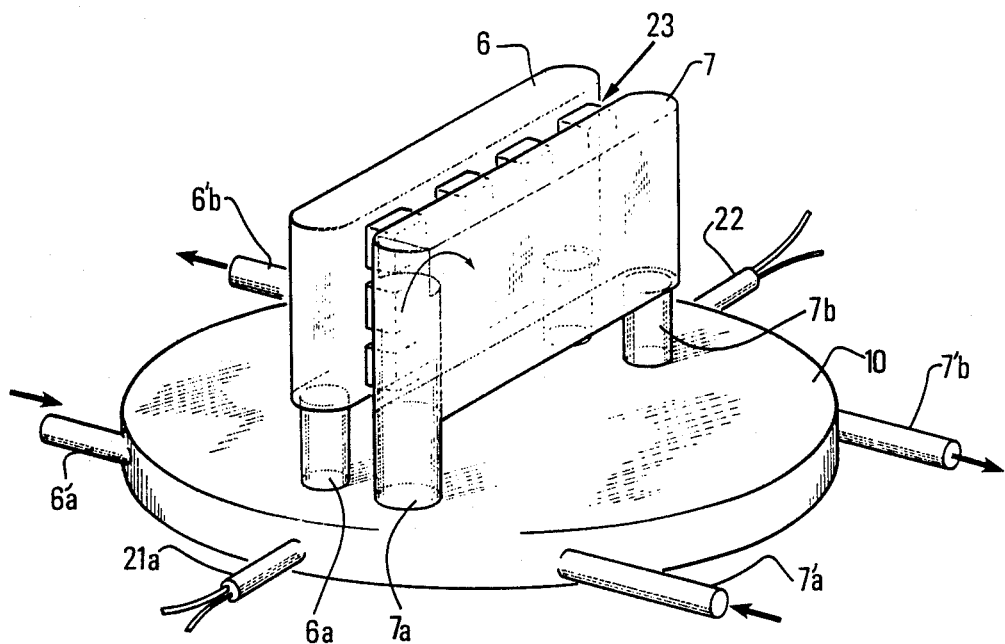
FIG. 4, is a perspective view of two cells mounted on a support place as well as supply pipes for each cells and for measurement probes.

As shown in FIG. 1, a calorimeter generally designated by the reference numeral 1 comprises a calorimetric casing generally designated by the reference numeral 2 containing a cold source generally designated by the reference numeral 3, a hot source generally designated by the reference numeral 4, and a calorimetric head generally designated by the reference numeral 5 including cells 6, 7.

The cold source 3 is fed with liquid nitrogen 18. A reservoir or cylinder 8 (FIG. 7) contains a resistance 9 supplied with a suitable power for maintaining a constant pressure, independent of the flowrate. A safety device for the nitrogen level may complete this assembly. The calorimetric casing 2 may be made simply, but non limitatively, from glass and may comprise two parts 11 and 12 and so be able to open completely, with sealing thereof being provided by an O-ring seal 13. The calorimetric casing 2 is provided with a cold nitrogen inlet 14 and the associated outlet 15, a vacuum cock generally designated by the reference numeral 16 and a sealed opening generally designated by the reference numeral 17 for the passage of the measurement and control wires, and the pipes through which the liquid to be analyzed flows into and out of the calorimetric head 5. In FIG. 1, the sealed opening 17 has been shown in the upper part 14 of calorimetric casing 2, but the sealed opening 17 may advantageously be placed in the lower part 12 of the calorimetric casing 2, so as to supply the calorimetric head 5.

The nitrogen 18 cools a copper plate 19 welded to the glass tube 21. This copper plate 19, which plays the role of cold source 3, receives a printed circuit heating resistance 20 which forms the hot source 4. Over this printed circuit is mounted a copper plate 10, forming a base for the cells 6,7 which may be identical to the first copper plate 10. This copper plate 10 may be termed oven, for it transmits to the calorimetric head 5 the heat coming from the heating resistance 20. The copper plate 10 (FIG. 4) comprises two platinum PT 100 probes, 21A and 22, with four wires, one of which may serve for temperature regulation and the other for the measurement. The embodiment described corresponds to differential coupled cell assemblies.

A measurement thermopile generally designated by the reference numeral 23, e.g. of the type 801-3960-01-00-00 commercialized by the firm called CAMCOOL MODULES receives on each face two sealed cells 6 and 7, preferably of the same dimensions as the thermopile. Each cell 6,7 is connected to the oven 10 by two tubes (tubes 6a and 7a, 7b respectively) which thus provide a part of the heat transfer. Finally, these tubes 6a, 7a, 7b, after passing through the oven 10, are extended on the outside by extension tubes 7'a, 7'b, 6'a and 6'b. These extension tubes leave the casing through the sealed opening 17.

Thus, the sample may be changed without disturbing the cells 6,7 which may have a volume of about 300 μl. The platinum probe for measuring the temperature is placed as close as possible to the cell containing the product.

FIG. 2 shows a cell generally designated by the reference numeral 24 comprising a pipe 24a for intake of the fluid and a cell 24b for discharge of the fluid.

The cell 24 may comprise small plates 25 forming a baffle system providing good scavenging of the cell 29 when the liquid is transferred.

Pipes 24a and 24b may be extended in the cell substantially as far as lid 26. In this case, of course, the configuration of the baffle system will be reversed. This embodiment shown in FIG. 4 for tube 7a simplifies the manufacture of the cells and makes them more rigid.

In FIG. 3, the system of pipes 7a, 7'a and 6a, 6'a through plate 10 has been shown with broken lines.

FIG. 6 shows one embodiment with three cells 27,28,29 for testing two products simultaneously by differential sweep microcalorimetry, with the cell 27 being a reference cell and the cells 28, 29 being measurement cells.

Between the reference cell 27 and each of the measurement cells 28 and 29 is placed a measurement thermopile (thermopiles 30 and 31 respectively).

In FIG. 1, the reference 32 designates the lid of the calorimetric head 5, with the lid 32 forming a thermal screen.

FIG. 5 shows an improvement of the calorimetric head in which an intermediate screen 33 is connected to the lid 32 by a thermopile 34. This thermopile 34 may be servo-controlled to maintain the screen 33 at the same temperature as the second copper plate 10. Thus, the heat exchanges between the cells 6 and 7 and the intermediate screen 33 are reduced to a minimum.

The vacuum cock 16 (FIG. 1) permits the evacuation of calorimetric casing 2, which reduces the heat exchanges between the calorimetric head and the walls of calorimetric casing 2.

The device of the invention is based on the principle that when a temperature range is swept in an enclosure containing a liquid, it can be seen that the temperature of the liquid follows with a certain lag the temperature rise of the enclosure, at least as long as there is no change of state within the liquid. If a change of state occurs in the liquid, then its temperature no longer follows that of the enclosure, at least as long as this change of state has not finished. It is the detection of the divergence of the temperature of the liquid with respect to that of the enclosure which informs about the change of state which is taking place in the liquid. This method, which only requires a single cell, forms what is called sweep microcalorimetry.

In the embodiment described, differential sweep microcalorimetry devices have been considered.

In microcalorimetry, it is necessary to have a measurement cell, for example cell 6, and a reference cell, for example cell 7, with the two cells 6,7 preferably having the same thermal characteristics. In the measurement cell 6 is introduced the liquid to be tested and in the reference cell 7 a reference fluid having preferably the same thermal characteristics as the fluid to be tested, but having no change of state in the swept temperature range. The difference of temperature between the two cells 6,7 is measured. This difference is small, if not zero, at least as long as there is no change of state in the fluid to be tested.

When there is a change of state in the fluid to be tested, a temperature difference is detected which makes it possible to detect the temperature at which this change of state occurs.

The device of the invention allows this procedure to be automated for the evaluation of several samples.

Figure 7:
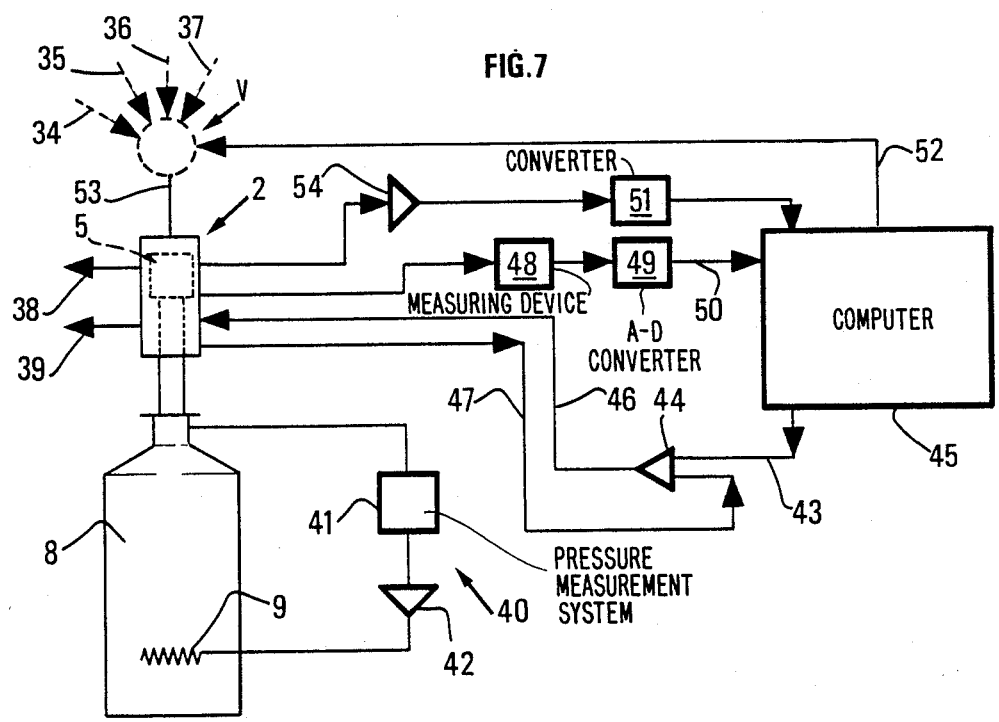
FIG. 7 is a schematic view of a detecting and/or measuring device of the present invention with automation means.

FIG. 7 shows a set-up allowing such automation.

A multi-way valve generally designated by the reference character V is provided for feeding the measurement cell with the fluids to be tested. This valve may be controlled by line 52 connected to the computer 45. The liquid may also be injected directly into line 53, e.g. by means of a syringe. When one of the fluids to be tested is conveyed over one of the ways 34, 35, 36 and 37, this fluid drives out the old fluid through the pipe 38.

In order to obtain good results it is preferable for the fluid to flow in the cell only during the test period. This may be guaranteed by using a member, possibly controllable, for closing off the pipes supplying the cell and/or emptying it. In this case, it will be possible, if required, to use a buffer volume for compensating the possible volume variations of the product.

Arrow 39 corresponds to reference 15 in FIG. 1 and so to discharge of the nitrogen.

Reference 40 designates an electronic circuit for regulating the pressure at the outlet of the liquid nitrogen cylinder or reservoir 8.

A system 41 comprising a mercury pressure gauge measure this pressure.

A photodiode concealed by the level of the mercury controls, through an element 42, the electric power fed to a resistance 9 immersed in the liquid nitrogen. For reasons of safety, the heating is maximum if the photodiode is illuminated.

Reference 43 designates the line which supplies to a differential amplifier 44 the reference temperature controlled by computer 45. Amplifier 44 delivers to the oven through line 46 the power required for obtaining the reference temperature controlled by the computer. Regulation of this temperature is provided over line 47 which is connected to one of the temperature probes of the oven. The temperature of the oven may be measured by means of a four wire assembly with current generator (1 mA) of the measurement probe PT 100 and comprising for example an instrumentation amplifier AD 522 S.

Thus, regulation of the temperature of the oven may comprise a pre-amplifier, probe PT 100 being fed with constant current, an amplifier 44 amplifying the difference between the measurement of the oven temperature and the reference from the D-A converter and a power amplifier.

The temperature of the calorimeter may be measured in the same way. Reference numeral 48 designates the device for measuring the temperature of the platinum probe and reference numeral 49 designates an A-D converter which may be of the digital voltmeter type DM-4100 D commercialized by the firm Datel.

This A-D converter 49 delivers to the computer over line 50 information relating to the temperature of the oven.

A converter 51 of the same type supplies to computer 45 the signal of the calorimeter coming from the thermopile 23 situated between the two cells 6 and 7.

Before reaching converter 51, this signal may be processed by an amplifier 54, for example, of the chopper 260K amplifier type commercialized by the firm Analog Device.

The computer may be of the type HP 85 commercialized by Hewlett Packard, completed by inlet-outlet cards, called BCD. The computer 45, under the control of its program, reads the temperature suggested by the line 50 and the temperature state of the calorimeter supplied from the connector 51 and controls a filling of the cell 6 with the first sample, then sends adequate orders to the temperature programmer 44, the test then takes place, for example, with cooling by 0.5° C./min and the computer effects data acquisition. With a thermal effect detected, it continues the acquisition of the measurements over a given time or temperature interval, then it resets the calorimeter to the starting temperature and starts analysis of the measurement. Finally, it controls the inlet of the next sample, and may proceed with a new determination.

The apparatus described makes it possible to determine the cloud point of gas-oils by using the thermal crystallization effect, without requiring an operator specialized in calorimetry. For measurements always taking place under the same conditions, particularly in the same temperature range, without departing from the scope of the present invention, cold sources may be used other than liquid nitrogen. The important advantage of the cooling mode described resides in the possibility of going down to very low temperatures, so as to accede to complementary information concerning the product and, in particular, its fine analysis, for example:

(a) the vitreous transition temperature (TG) of the hydrocarbonated matrix;

(b) the n-paraffin content (% by weight) contained in the product studied;

(c) distribution of the paraffins by classes, or even individually, as present day work suggests.

A temperature of 150K was reached without difficulty and it seems possible to reach 120K.

What is claimed is:

1. A device for detecting and/or measuring a thermal phenomenon occurring in a product having a liquid state at a temperature within a range of temperatures swept by the detecting and/or measuring device, comprising an enclosure means for accommodating a calorimetric head means including at least one measurement cell means and a reference cell means, means for transferring heat to said at least one measurement cell means, means for measuring a differential magnitude related to a temperature of said at least one measurement cell means, means for filling said at least one measurement cell and the reference cell means with liquid and emptying said cell means of said liquid, and means for adjusting a temperature of the enclosure means by changing the enclosure temperature within a predetermined temperature range.

2. The device as claimed in claim 1, comprising at least two measurement cell means.

3. The device as claimed in claim 1, comprising at least one fluxmeter means disposed between the at least one measurement cell means and the reference cell means.

4. The device as claimed in claim 3, wherein said at least one measurement cell means includes a thermopile.

5. The device as claimed in claim 1, wherein said at least one measurement cell means is placed on a base means made from a material having good heat conducting characteristics.

6. The device as claimed in claim 5, wherein said base means comprises at least a portion of a circuit means for supplying said at least one measurement cell means with liquid.

7. The device as claimed in claim 6, wherein said base means is in contact with said heat transferring means.

* * * * *